United States Patent [19]

Gubernick

[11] 4,005,210
[45] Jan. 25, 1977

[54] PROTEIN CONTAINING EMOLLIENT COMPOSITION FOR A SKIN MOISTURIZER

[75] Inventor: Joseph Gubernick, Port Washington, N.Y.

[73] Assignee: Estee Lauder, Inc., New York, N.Y.

[22] Filed: July 3, 1975

[21] Appl. No.: 593,136

[52] U.S. Cl. .............................. 424/359; 424/365
[51] Int. Cl.² .................................... A61K 7/48
[58] Field of Search ........................ 424/359, 365

[56] References Cited

UNITED STATES PATENTS

| | | | |
|---|---|---|---|
| 3,424,849 | 6/1969 | Conklin et al. | 424/365 |
| 3,535,427 | 10/1970 | Millar et al. | 424/365 |
| 3,660,566 | 5/1972 | Vinson et al. | 424/359 |
| 3,835,169 | 9/1974 | Kraft et al. | 424/365 X |
| 3,941,722 | 3/1976 | Shevlin | 424/359 X |

*Primary Examiner*—Albert T. Meyers
*Assistant Examiner*—Vera C. Clarke
*Attorney, Agent, or Firm*—Blum Moscovitz Friedman & Kaplan

[57] ABSTRACT

An emollient composition which has utility as a skin moisturizer comprises from about 2 to about 20% isodecyl neopentanoate, from about 0.25 to 2% oleolyl polypeptide, and up to 97% mineral oil.

2 Claims, No Drawings

PROTEIN CONTAINING EMOLLIENT COMPOSITION FOR A SKIN MOISTURIZER

BACKGROUND OF THE INVENTION

The instant invention relates to an emollient composition and more particularly to an emollient composition that is a skin moisturizer.

Excessive use of soap and water removes natural oils and secretions from human skin. Unless these natural oils and secretions are replaced, human skin becomes dry, scaly and loses its youthful appearance.

In a high aseptic society of the type in this country, there is a need for a skin moisturizer that artificially replaces natural skin oils which are cleansed away. This invention provides an emollient composition which artificially moisturizes human skin to restore its vibrancy and youthful appearance.

SUMMARY OF THE INVENTION

Generally speaking, in accordance with the invention, an emollient composition is provided which comprises from about 2 to about 20% isodecyl neopentanoate, from about 0.25 to 2% oleolyl polypeptide, and up to 97% mineral oil. It is found that an emollient composition formulated within these proportions is a skin moisturizer.

Accordingly, it is an object of the invention to provide an emollient composition that moisturizes skin.

Another object of the invention is to provide a composition that is suitably absorbed by human skin for moisturizing human skin.

Still other objects and advantages of the invention will in part be obvious and will in part be apparent from the specification.

The invention accordingly comprises a composition of matter possessing the characteristics, properties, and the relation of components which will be exemplified in the composition hereinafter described, and the scope of the invention will be indicated in the claims.

DETAILED DESCRIPTION OF THE INVENTION

Emollient compositions within the scope of the invention show significant penetration into human skin with the attendant cosmetic benefit of protein absorption. The active ingredient within the composition is isodecyl neopentanoate and from about 2 to about 20% thereof may be employed in the composition. However, a preferred composition includes 2% isodecyl neopentanoate. The isodecyl neopentanoate is believed to condition human skin for penetration of protein therein.

A typical protein that may be included in the composition is hydrolyzed animal protein. Among the most preferred hydrolyzed animal protein is oleolyl polypeptide. Preferably from about 0.25 to 2% thereof is included in the composition. In a most preferred composition about 1% oleolyl polypeptide is included in the composition.

Various petrolatums are suitable carriers for the protein and active skin conditioning ingredient. The most preferred petrolatum is mineral oil. Preferably, the remainder of the composition comprises mineral oil. Therefore, in the most preferred composition up to 97% of the composition may be mineral oil.

The components of the composition may be formulated according to conventional admixing techniques. For instance, the components may be consecutively added to a mixing vessel and admixed under agitation. The method for formulating the composition is not critical.

It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An emollient composition comprising from about 2 to about 20% isodecyl neopentanoate, from about 0.25 to 2% oleolyl polypeptide which is a hydrolyzed animal protein, and up to 97% mineral oil.

2. The emollient composition as claimed in claim 1, wherein the content of oleolyl polypeptide is about 1%.